United States Patent [19]

Feit et al.

[11] 4,018,794
[45] Apr. 19, 1977

[54] SULFAMYLBENZOIC ACID DERIVATIVES

[75] Inventors: Peter Werner Feit, Gentofte; Ole Bent Tvaermose Nielsen, Vanlose, both of Denmark

[73] Assignees: Leo Pharmaceutical Products Ltd.; A/S Lovens Kemiske Fabrik Produktionsaktieselskab, both of Ballerup, Denmark

[22] Filed: Feb. 19, 1975

[21] Appl. No.: 551,147

Related U.S. Application Data

[62] Division of Ser. No. 349,826, April 10, 1973, Pat. No. 3,897,476.

[30] Foreign Application Priority Data

Apr. 28, 1972 United Kingdom .............. 19959/72
Nov. 16, 1972 United Kingdom .............. 53043/72

[52] U.S. Cl. ................. 260/332.2 A; 260/290 HL; 260/294.8 E; 260/295 AM; 260/297 R; 260/302 F; 260/304 R; 260/329 S; 260/332.3 R; 260/332.5; 260/347.2; 260/347.3; 260/347.8; 260/515 R; 260/515 A; 260/515 M; 424/232; 424/270; 424/275; 424/285

[51] Int. Cl.² ........................................ C07D 333/24
[58] Field of Search .................. 260/329 S, 332.2 A

[56] References Cited

OTHER PUBLICATIONS

Feit, "Journal of Medicinal Chem", (1974), vol. 17, No. 6, pp. 572–578.

*Primary Examiner*—James O. Thomas, Jr.
*Assistant Examiner*—A. Siegel
*Attorney, Agent, or Firm*—Jackson, Jackson and Chovanes

[57] ABSTRACT

Compounds of the general formulae

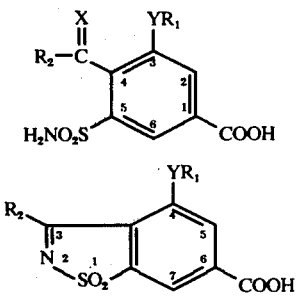

in which $R_1$ represents a straight or branched, optionally substituted alkyl, alkenyl or alkynyl radical; $R_2$ stands for an optionally substituted phenyl radical; Y stands for oxygen, sulphur or a methylene radical; X stands for O or $H_2$; their salts and esters and methods for their preparation.

The compounds of the invention possess an outstanding diuretic and saluretic activity with a very low excretion of potassium ions and a low toxicity.

5 Claims, No Drawings

SULFAMYLBENZOIC ACID DERIVATIVES

This is a division of Ser. No. 349,826, filed Apr. 10, 1973 now U.S. Pat. No. 3,897,476.

This invention relates to a series of new compounds, their salts and esters and to methods for the preparation of the compounds having the general formula:

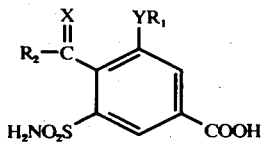

in which $R_1$ represents a straight or branched $C_1-C_6$ alkyl, alkenyl or alkynyl radical, or a $C_1-C_3$ alkyl radical substituted with phenyl, halophenyl, trifluoromethylphenyl, (lower alkoxy)phenyl, or with a 5-membered or 6-membered heterocyclic ring containing not more than two heteroatoms selected from the group consisting of oxygen, sulphur and nitrogen; $R_2$ stands for a phenyl radical, optionally being substituted with halogen, lower alkyl, hydroxy, or lower alkoxy; Y stands for oxygen, sulphur or a methylene radical; X stands for O or $H_2$.

In the case of X being O, the compounds of the invention also include compounds of formula II

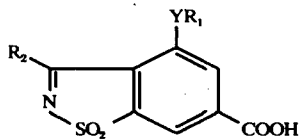

in which $R_1$, $R_2$ and Y have the above meaning, which are obtained by simple dehydration. This dehydration is a reversible process.

In particular, $R_1$ may represent e.g. a methyl, ethyl, propyl, isopropyl, butyl, isobutyl or tert. butyl radical, or one of the different isomeric pentyl, or hexyl radicals, an alkenyl or alkynyl radical, e.g. an allyl, or propargyl radical, a benzyl or phenethyl radical, a 2-, 3-, or 4-pyridylmethyl, 2- or 3-furylmethyl, 2- or 3-thienylmethyl, thiazolylmethyl, or imidazolylmethyl radical; or one of the corresponding ethyl radicals.

Of particular value are the compounds of the invention in which $R_1$ is selected from the group consisting of straight or branched $C_3-C_5$ alkyl radicals, and a methyl radical being substituted with phenyl, furyl, thienyl, and pyridyl, and the correspondingly substituted ethyl radicals.

The substituents $R_1$ and $R_2$ of formulae I and II can be further substituted in different positions with different groups, such as one or more halogen atoms, e.g. chlorine or bromine atoms, lower alkyl, halo-lower alkyl, e.g. trifluoromethyl; hydroxy groups, which may be etherified, e.g. lower alkoxy, such as methoxy, ethoxy, n-propoxy, isopropoxy, n-butoxy or isobutoxy, or esterified with lower aliphatic carboxylic acids, such as lower alkanoic acids, e.g. acetic, propionic or pivalic acid, lower alkenoic acids, e.g. acrylic or methacrylic acid, or with lower aliphatic dicarboxylic acids, e.g. oxalic, malonic, succinic, glutaric, adipic, maleic or fumaric acid or their acid esters with lower alkanols, e.g. methanol or ethanol; or etherified mercapto groups such as methylthio, ethylthio, isopropylthio, butylthio or isobutylthio radicals.

Whenever the expression "lower alkyl" is used in the foregoing and in the following it stands for a straight or branched alkyl radical with from 1 to 6 carbon atoms in the chain.

The salts of the compounds of the invention are pharmaceutically acceptable salts, and include, for example, alkali metal salts, alkaline earth metal salts, the ammonium salt, or amine salts formed, for instance, from mono-, di- or trialkanolamines or cyclic amines. The esters of the compounds are preferably derived from lower aliphatic alcohols, cyanomethanol and benzyl alcohol.

It has surprisingly been found that the compounds of the invention possess an outstanding diuretic and saluretic activity with a very low excretion of potassium ions and a low toxicity which make the present compounds particularly valuable in human or veterinary practice.

In the present series of compounds, the position of the $YR_1$ group is essential, as according to experiments performed in connection with the present invention, it has been found that the compounds of the following formula

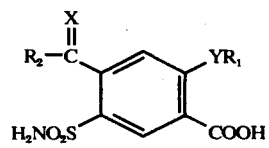

in which $R_1$, $R_2$, X and Y have the above meaning, and in which the $YR_1$ group is placed in the 2-position have a negligible diuretic effect.

The compounds of the invention are more stable than the known benzoic acid derivatives containing an amino or substituted amino group, e.g. furosemide, which are light-sensitive and must be stored in dark receptacles.

Further the compounds of the invention are also extremely valuable in the treatment of patients suffering from hypersensitivity towards sulfanilamide diuretics and metanilamide diuretics because there exists no cross hypersensitivity between these compounds and the compounds of the invention.

The present compounds are effective after oral, enteral or parenteral administration, and are preferably prescribed in the form of tablets, pills, gragees, or capsules containing the free acid or salts thereof with atoxic bases, or the esters thereof, mixed with carriers and/or auxiliary agents.

Salts, which are soluble in water, may with advantage be administered by injection. The compounds of the invention are useful in the treatment of oedematous conditions e.g. cardiac, hepatic, renal, lung, and brain oedema, or oedematous conditions during pregnancy, and of pathological conditions which produce an abnormal retension of the electrolytes of the body, and in the treatment of hypertension.

Another object of the invention resides in the selection of a dose of one of the compounds of the invention or their salts or esters which can be administered so that the desired activity is achieved without simultaneous secondary effects. In such a dosage unit the compounds are conveniently administered as a pharmaceutical preparation containing from 0.1 mg to 25 mg of the active compound. The compounds of formula I are preferably administered in amounts from 0.5 mg to 10 mg. By the term "dosage unit" is meant a unitary, i.e. a single dose capable of being administered to a patient, and which may be readily handled and packed, remaining as a physically stable unit dose, comprising either the active material as such or in a mixture of it with a pharmaceutical carrier and auxiliary agents.

In the form of a dosage unit the compounds may be administered one or more times a day at appropriate intervals. The daily dose usually amounts to from 0.5 to 50 mg always depending, however, on the condition of the patients and according to the prescription of the medical practitioner.

In pharmaceutical compositions containing the compounds of the invention, organic or inorganic, solid or liquid carriers suitable for oral, enteral, or parenteral administration can be used to make up the composition. Gelatine, lactose, starch, magnesium stearate, talc, vegetable and animal fats and oils, gum, polyalkylene glycol, or other known carriers for medicaments are all suitable as carriers.

In the pharmaceutical compositions, the proportion of therapeutically active material to carrier substances can vary between 0.5 percent and 90 percent.

The compositions may further contain other therapeutic compounds applied in the treatment of, for example oedemas and hypertension, besides the well-known auxiliary agents. Such other compounds may be, for instance, Veratrum- or Rauwolfia alkaloids, e.g. reserpine, rescinnamine or protoveratrine or synthetic hypotensive compounds, e.g. hydralazine, or other diuretics and saluretics, such as the well-known benzothiadiazines, e.g. hydroflumethiazide, bendroflumethiazide, and the like. Potassium-sparing diuretics, e.g. triamterene, may also be used in the preparation of the compositions. For some purposes it may be desirable to add small amounts of aldosterone antagonists, e.g. spironolactone.

It is another object of the invention to provide methods of preparing the compounds of the invention.

In one embodiment the compounds of the invention are prepared according to the following reaction scheme

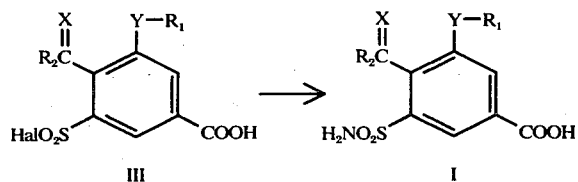

in which formulae the substituents $R_1$, $R_2$, X and Y are as defined before, and Hal stands for a halogen atom, preferably chlorine. The reaction is performed by treating the compound of formula III with ammonia, either with liquid ammonia or preferably concentrated aqueous ammonia, or under reaction conditions where ammonia is liberated, such as treatment with ammonium carbonate, if necessary by heating. The isolation of the compounds of formula I can be performed by means of well-known standard procedures.

When esters of the compounds of the formula III are used in the reaction, the compounds of the formula I are obtained as esters, or in some cases due to an aminolysis as amides. The corresponding free acids may, optionally, be obtained by a subsequent saponification. In case of the desired product being an ester and the starting material of formula III being the free acid, an esterification can be performed either before or after the amidation process.

Since the compounds of formula I in which X stands for oxygen are dehydrated at elevated temperatures to give the compounds of formula II as defined before, the melting points of the former compounds are not well defined and these compounds can therefore appropriately be characterized by means of their IR spectra, having absorption bands due to the hydrogens situated at the sulfamyl nitrogen and to the diaryl carbonyl group. The benzisothiazol dioxides of formula II have reproducible and characteristic melting points and they are further characterized by means of their IR spectra (lacking the above mentioned absorption bands).

The compounds of formula II are easily prepared by dehydration. The dehydration process of the corresponding compounds of formula I (X = O) can be performed under various reaction conditions, e.g. by melting, or under conditions where the water formed during the reaction is removed under reduced pressure or by means of azeotropic distillation or by a dehydrating agent such as sulfuric acid or phosphorous pentoxide.

The starting compounds of formula III can e.g. be prepared through several steps from compounds of formula IV

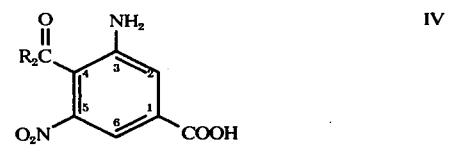

in which $R_2$ has the above meaning, which compounds are known.

The 3-amino group in the compounds of formula IV is diazotized, and the diazonium salt solution is heated, if necessary, under acidic conditions to give the corresponding 4-$R_2$CO-3-hydroxy-5-nitrobenzoic acid. When the corresponding 3-mercapto derivative is desired, the above mentioned diazonium salt, if convenient after isolation and purification as e.g. a diazoniumtetrafluoroborate or a diazoniumchloride, is reacted with e.g. potassium ethyl xanthate or with potassium thiocyanate in the presence of copper thiocyanate or with an alkali disulfide followed by either a saponification or a reduction, dependent on the reactant used in the process.

When the corresponding 4-$R_2$CO-3-$R_1$CH$_2$-5-nitrobenzoic acid is desired, the above mentioned diazonium salt is reacted with the appropriate alkene in known manner, the resulting 3-alkene-4-$R_2$CO-5-nitrobenzoic acid thereafter being hydrogenated to the corresponding compound included in the general formula V

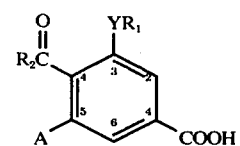

in which $R_1$, $R_2$, and Y have the above meanings, and A, depending on the reaction conditions used, is a nitro group, an amino group, or a group resulting from the formation of an intermediate during the reduction of $A = NO_2 = NH_2$, in which cases the compounds of formula V represent the corresponding azo or hydrazo compounds. The above mentioned 3-hydroxy or 3-mercapto derivatives of the 4-$R_2$CO-5-nitrobenzoic acids are, if convenient without isolation, alkylated, to the corresponding compounds of the above general formula V.

Appropriately the alkylation can be performed either on the free acid or on one of its esters by treatment with a compound $R_1Z$ in which $R_1$ has the above meaning and Z stands for a halogen atom, or an alkyl- and arylsulphonyloxy group, or with a di-$R_1$-sulphate, a diazo compound of the formula $R_1N_2$, or a quaternary ammonium compound of the formula $R_1N^+(Alk)_3$, in which $R_1$ has the above meaning and Alk stands for alkyl with from 1 to 6 carbon atoms.

The compounds of formula V in which Y is oxygen or sulphur and A is a nitro group can also be prepared by reacting the above mentioned diazonium salts with a compound of the formula $F_1YH$, in which $P_1$ is as defined above and Y is oxygen or sulphur.

When A is different from $NH_2$, the compounds of the formula V are then reduced to compounds containing an amino group in the 5-position, for instance with an excess of sodium dithionite or with ferrous salts or iron powder or with stannous chloride and, if desired, the 4-$R_2$CO group is reduced to a 4-$R_2CH_2$ group, e.g. by a Wolff-Kishner reduction. The reduction of the A- group in the 5-position and the keto group in the 4-position can be performed simultaneously, e.g. by means of a Wolff-Kishner reduction.

The 5-amino-4-$R_2$CX-3-$YR_1$-benzoic acids thus obtained are thereafter through their corresponding diazonium salts and by means of the well-known Meerwein-reaction transferred into the corresponding 5-halosulfonyl derivatives of the general formula III.

The reactions described above for the production of the starting materials of formula III can be performed in arbitrary order. For instance can the reduction of the 5-nitro group and/or of the 4-keto group be performed before or simultaneously with the alkylation of the 3-YH group. All these reactions are well-known to the skilled chemist, and the reaction products are easily isolated, In another embodiment, the reduction of the compounds of formula I in which X stands for oxygen to the compounds in which X stands for hydrogen is performed as the last step, i.e. after the introduction of the 5-sulfamyl group.

In still another embodiment the compounds of the invention are prepared by reacting a diazonium salt of a compound of formula VI or an ester thereof

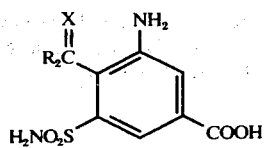

in which $R_2$ and X are as defined above with a compound of the formula $R_1YH$ in which $R_1$ is as defined above and Y stands for oxygen and sulphur, or with an appropriate alkene, in the latter case followed by hydrogenation of the alkene group thus introduced in the 3-position.

The starting materials of formula VI in which X is $H_2$ are known compounds. The compounds of formula VI in which X is oxygen are easily available by alkaline treatment of the corresponding known benzisothiazoles of formula VII

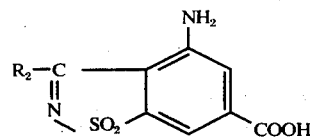

in which $R_2$ is as defined above.

In still another embodiment compounds of the invention in which Y is oxygen or sulphur are prepared by alkylation of a compound of formula VIII

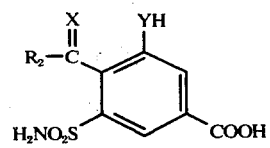

in which $R_2$ and X are as defined above and Y is oxygen or sulphur, with a compound of the formula $R_1Z$ as defined and described above for the preparation of the compounds of formula V. The starting compounds of formula VIII can be prepared from the diazonium salts of the compounds of formula VI by well-known reactions described above in the present application.

The invention will now be illustrated by the following non-limiting Examples from which the details of the embodiments will be apparent.

EXAMPLE 1

4-Benzoyl-3-n-butoxy-5-chlorosulfonylbenzoic acid

A. 4-Benzoyl-3-hydroxy-5-nitrobenzoic acid.

To a solution of 3-amino-4-benzoyl-5-nitrobenzoic acid (100 g) in a mixture of conc. sulfuric acid (875 ml) and water (280 ml) is dropwise added a solution of sodium nitrite (45.0 g) in water (280 ml), while stirring at −5° C to 0° C. After additional stirring at −5° C to 0° C for about 15 minutes, the resulting diazoniumsolution is heated on a steam bath for 2–3 hours until the nitrogen evolution has ceased. After cooling, the resulting precipitate is collected by filtration and washed with water. After drying and recrystallization twice from aqueous ethanol, 4-benzoyl-3-hydroxy-5-nitrobenzoic acid is obtained as a monohydrate with a melting point of 264°–266° C.

B. 4-Benzoyl-3-n-butoxy-5-nitrobenzoic acid.

A stirred mixture of 4-benzoyl-3-hydroxy-5-nitrobenzoic acid (10.0 g), 7 N sodium hydroxide (10 ml), ethanol (150 ml), and n-butylbromide (20 ml) is heated on a steam bath for 20 hours. After cooling, the ethanol is removed in vacuo and the residue is dissolved in hot water. The solution is acidified with 4 N hydrochloric acid. After cooling, the resulting precipitate is collected by filtration and washed with water. The material is dissolved in a hot saturated sodium hydrogencarbonate solution (75 ml) and filtered hot in the presence of decolorizing carbon. After cooling, the precipitated sodium 4-benzoyl-3-n-butoxy-5-nitrobenzoate is collected by filtration and washed with a small amount of ice-cold water followed by ethanol. After drying, the sodium salt is dissolved in hot water (100 ml), and the 4-benzoyl-3-n-butoxy-5-nitrobenzoic acid is precipitated by addition of conc. hydrochloric acid (5 ml). After cooling, the acid is collected by filtration, washed with water and dried. After recrystallization twice from aqueous ethanol, it is obtained with a melting point of 183°–185° C.

C. 5-Amino-4-benzoyl-3-n-butoxybenzoic acid.

To a stirred mixture of 4-benzoyl-3-n-butoxy-5-nitrobenzoic acid (5.1 g), pyridine (25 ml), and water (25 ml), sodium dithionite (10.2 g) is added in portions. The mixture is heated on a steam bath for 1 hour and is then evaporated in vacuo. The remaining material is dissolved in water (about 50 ml) and the solution is acidified with conc. hydrochloric acid (about 15 ml). After cooling, the resulting precipitate is collected by filtration and washed with water. After drying and recrystallization twice from ethanol, 5-amino-4-benzoyl-3-n-butoxybenzoic acid is obtained with a melting point of 202.5°–203.5° C.

D. 4-Benzoyl-3-n-butoxy-5-chlorosulfonylbenzoic acid.

A mixture of 5-amino-4-benzoyl-3-n-butoxybenzoic acid (1.15 g) and conc. hydrochloric acid (15 ml) is heated on a steam bath for about 10 minutes and is then cooled. The amine is diazotized by dropwise addition of a solution of sodium nitrite (0.28 g) in water (2.0 ml), while stirring at 0°–5° C. The resulting diazonium-mixture is poured into a solution of cupric chloride dihydrate (0.25 g) in water (1.0 ml) and acetic acid (15 ml) saturated with $SO_2$, while stirring at room temperature. The stirring is continued for 1 hour and the mixture is then diluted with water (about 15 ml). The precipitated 4-benzoyl-3-n-butoxy-5-chlorosulfonylbenzoic acid is collected by filtration, washed with water and dried.

EXAMPLE 2

4-Benzoyl-5-chlorosulfonyl-3-n-propoxybenzoic acid

A. Benzoyl-5-nitro-3-n-propoxybenzoic acid.

By replacing in Example 1, step B, n-butylbromide with n-propylbromide and following the procedure described, 4-benzoyl-5-nitro-3-n-propoxybenzoic acid is obtained with a melting point of 160.5°–162° C.

B. 5-Amino-4-benzoyl-3-n-propoxybenzoic acid.

By replacing in Example 1, step C, 4-benzoyl-3-n-butoxy-5-nitrobenzoic acid with 4-benzoyl-5-nitro-3-n-propoxybenzoic acid and following the procedure described, 5-amino-4-benzoyl-3-n-propoxybenzoic acid is obtained with a melting point of 220°–222° C.

C. 4-Benzoyl-5-chlorosulfonyl-3-n-propoxybenzoic acid

By replacing in Example 1, step D, 5-amino-4-benzoyl-3-n-butoxybenzoic acid with 5-amino-4-benzoyl-3-n-propoxybenzoic acid, and following the procedure described, 4-benzoyl-5-chlorosulfonyl-3-n-propoxybenzoic acid is obtained.

EXAMPLE 3

4-Benzoyl-5-chlorosulfonyl-3-n-pentyloxybenzoic acid

A. 4-Benzoyl-5-nitro-3-n-pentyloxybenzoic acid.

By replacing in Example 1, step B, n-butylbromide with n-pentylbromide, and following the procedure described, 4-benzoyl-5-nitro-3-n-pentyloxybenzoic acid is obtained with a melting point of 163°–165° C.

B. 5-Amino-4-benzoyl-3-n-pentyloxybenzoic acid

By replacing in Example 1, step C, 4-benzoyl-3-n-butoxy-5-nitrobenzoic acid with 4-benzoyl-5-nitro-3-n-pentyloxybenzoic acid and following the procedure described, 5-amino-4-benzoyl-3-n-pentyloxybenzoic acid is obtained with a melting point of 168.5°–170° C.

C. 4-Benzoyl-5-chlorosulfonyl-3-n-pentyloxybenzoic acid.

By replacing in Example 1, step D, 5-amino-4-benzoyl-3-n-butoxybenzoic acid with 5-amino-4-benzoyl-3-n-pentyloxybenzoic acid and following the procedure described, 4-benzoyl-5-chlorosulfonyl-3-n-pentyloxybenzoic acid is obtained.

EXAMPLE 4

4-Benzoyl-3-benzyloxy-5-chlorosulfonylbenzoic acid

A. 4-Benzoyl-3-benzyloxy-5-nitrobenzoic acid.

By replacing in Example 1, step B, n-butylbromide with benzylbromide, and following the procedure described, 4-benzoyl-3-benzyloxy-5-nitrobenzoic acid is obtained with a melting point of 205°–207° C.

B. 5-Amino-4-benzoyl-3-benzyloxybenzoic acid

By replacing in Example 1, step C, 4-benzoyl-3-n-butoxy-5-nitrobenzoic acid with 4-benzoyl-3-benzyloxy-5-nitrobenzoic acid, and following the procedure described, 5-amino-4-benzoyl-3-benzyloxybenzoic acid is obtained with a melting point of 216.5°–217.5° C.

C. 4-Benzoyl-3-benzyloxy-5-chlorosulfonylbenzoic acid.

By replacing in Example 1, step D, 5-amino-4-benzoyl-3-n-butoxy-benzoic acid with 5-amino-4-benzoyl-3-benzyloxybenzoic acid, and following the procedure described, 4-benzoyl-3-benzyloxy-5-chlorosulfonylbenzoic acid is obtained.

EXAMPLE 5

4-Benzoyl-5-chlorosulfonyl-3-(2-phenethoxy)benzoic acid

A. 4-Benzoyl-5-nitro-3-(2-phenethoxy)benzoic acid.

By replacing in Example 1, step B, n-butylbromide with 2-phenylethylbromide, and following the procedure described, 4-benzoyl-5-nitro-3-(2-phenethoxy)-benzoic acid is obtained with a melting point of 168.5°–170.5° C.

B. 5-Amino-4-benzoyl-3-(2-phenethoxy)benzoic acid.

By replacing in Example 1, step C, 4-benzoyl-3-n-butoxy-5-nitrobenzoic acid with 4-benzoyl-5-nitro-3-(2-phenethoxy)benzoic acid, and following the procedure described, 5-amino-4-benzoyl-3-(2-phenethoxy)-benzoic acid is obtained as a semi-hydrate with a melting point of 162°–163° C.

C. 4-Benzoyl-5-chlorosulfonyl-3-(2-phenethoxy)-benzoic acid.

By replacing in Example 1, step D, 5-amino-4-benzoyl-3-n-butoxybenzoic acid with 5-amino-4-benzoyl-3-(2-phenethoxy)benzoic acid, and following the procedure described, 4-benzoyl-5-chlorosulfonyl-3-(2-phenethoxy)benzoic acid is obtained.

EXAMPLE 6

4-Benzoyl-5-chlorosulfonyl-3-ethoxybenzoic acid

A. Ethyl 4-benzoyl-3-hydroxy-5-nitrobenzoate.

A solution of 4-benzoyl-3-hydroxy-5-nitrobenzoic acid, monohydrate prepared as described in Example 1, step A, (100 g) in dry ethanol (2 liter) is evaporated in vacuo in order to remove the water of crystallization. The residue is redissolved in dry ethanol (2 liter), conc.

sulfuric acid (45 ml) is added and the solution is refluxed for 20 hours. The excess of ethanol is removed in vacuo, and the residue is triturated with a saturated sodium hyrogen carbonate solution (about 900 ml). The resulting material is collected by filtration and washed with water. After drying and recrystallization from aqueous ethanol, ethyl 4-benzoyl-3-hydroxy-5-nitrobenzoate is obtained with a melting point of 167°–168° C.

B. 4-Benzoyl-3-ethoxy-5-nitrobenzoic acid.

To a solution of sodium ethanolate (prepared from 1.3 g of sodium) in dry ethanol (125 ml), ethyl 4-benzoyl-3-hydroxy-5-nitrobenzoate (12.6 g) is added followed by ethyl iodide (4.0 ml), and the resulting solution is refluxed for 20 hours. After about 4 hours, an additional amount of sodium ethanolate (prepared from 0.65 g of sodium) in dry ethanol (65 ml) is added followed by ethyl iodide (2.0 ml). The mixture is evaporated in vacuo, 2 N sodium hydroxide (125 ml) is added to the residue, and the mixture is heated on a steam bath for 1 hour to form a clear solution. On cooling, sodium 4-benzoyl-3-ethoxy-5-nitrobenzoate seprates. It is collected by filtration, and washed with a small amount of ice-cold water followed by ethanol. After drying, the sodium salt is dissolved in hot water (100 ml), and the 4-benzoyl-3-ethoxy-5-nitrobenzoic acid is precipitated by addition of conc. hydrochloric acid (4 ml). After cooling, the acid is collected by filtration and washed with water. After drying and recrystallization from 96% ethanol, 4-benzoyl-3-ethoxy-5-nitrobenzoic acid crystallizing with 0.5 moles of ethanol is obtained with a melting point of 188°–191° C C. 5-Amino-4-benzoyl-3-ethoxybenzoic acid.

By replacing in Example 1, step C, 4-benzoyl-3-n-butoxy-5-nitrobenzoic acid with 4-benzoyl-3-ethoxy-5-nitrobenzoic acid, and following the procedure described, 5-amino-4-benzoyl-3-ethoxybenzoic acid is obtained with a melting point of 229.5°–230.5° C.

D. 4-Benzoyl-5-chlorosulfonyl-3-ethoxybenzoic acid.

A solution of 5-amino-4-benzoyl-3-ethoxybenzoic acid (2.56 g) and lithium nitrite hydrate (0.69 g) in 1 N lithium hydroxide (12 ml) is added dropwise to a mixture of conc. hydrochloric acid (30 ml) and acetic acid (30 ml), while stirring at 0° C to −5° C. The resulting diazonium solution is clarified by rapid filtration, and is then added to a solution of cupric chloride dihydrate (0.6 g) in water (3.0 ml) and acetic acid (30 ml) saturated with $SO_2$, while stirring at room temperature. After additional stirring for 2-3 hours, the precipitated 4-benzoyl-5-chlorosulfonyl-3-ethoxybenzoic acid is collected by filtration, washed with water and dried.

EXAMPLE 7

4-Benzoyl-5-chlorosulfonyl-3-n-hexyloxybenzoic acid

A. 4-Benzoyl-3-n-hexyloxy-5-nitrobenzoic acid.

By replacing in Example 6, step B, ethyl iodide with an equimolar amount of n-hexyl bromide, and following the procedure described, 4-benzoyl-3-n-hexyloxy-5-nitrobenzoic acid is obtained with a melting point of 165°–166° C.

B. 5-Amino-4-benzoyl-3-n-hexyloxybenzoic acid.

By replacing in Example 1, step C, 4-benzoyl-3-n-butoxy-5-nitrobenzoic acid with 4-benzoyl-3-n-hexyloxy-5-nitrobenzoic acid, and following the procedure described, 5-amino-4-benzoyl-3-n-hexyloxybenzoic acid is obtained with a melting point of 168°–169' C.

C. 4-Benzoyl-5-chlorosulfonyl-3-n-hexyloxybenzoic acid.

By replacing in Example 6, step D, 5-amino-4-benzoyl-3-ethoxybenzoic acid with 5-amino-4-benzoyl-3-n-hexyloxybenzoic acid, and following the procedure described, 4-benzoyl-5-chlorosulfonyl-3-n-hexyloxybenzoic acid is obtained.

EXAMPLE 8

4-Benzoyl-5-chlorosulfonyl-3-isobutoxybenzoic acid

A. 4-Benzoyl-3-isobutoxy-5-nitrobenzoic acid.

To a stirred solution of ethyl 4-benzoyl-3-hydroxy-5-nitrobenzoate (7.9 g) in hexamethyl phosphoric triamide (30 ml), sodium hydride (1.2 g of a dispersion 55–60% in oil) is added in portions. When the hydrogen evolution has subsided, isobutylbromide (5.0 ml) is added and the resulting solution is heated on a steam bath for about 20 hours. After cooling, the solution is diluted with water (40 ml) and is then acidified with conc. hydrochloric acid (5 ml). The precipitated oil is extracted with diethyl ether, and the extract is evaporated in vacuo. To the residue 2 N sodium hydroxide (45 ml) is added, and the mixture is heated on a steam bath for 30 minutes. The resulting solution is clarified by filtration hot in the presence of decolorizing carbon. On cooling sodium 4-benzoyl-3-isobutoxy-5-nitrobenzoate separates; the salt is collected by filtration and washed with a small amount of icecold water. The dried sodium salt is dissolved in hot water (50 ml) and 4-benzoyl-3-isobutoxy-5-nitrobenzoic acid is precipitated by addition of conc. hydrochloric acid (3 ml). After cooling, the acid is collected by filtration, washed with water and dried. After recrystallization twice from aqueous ethanol it is obtained with a melting point of 142°–145° C.

B. 5-Amino-4-benzoyl-3-isobutoxybenzoic acid.

By replacing in Example 1, step C, 4-benzoyl-3-n-butoxy-5-nitrobenzoic acid with 4-benzoyl-3-isobutoxy-5-nitrobenzoic acid, and following the procedure described, 5-amino-4-benzoyl-3-isobutoxybenzoic acid is obtained with a melting point of 192°–196° C.

C. 4-Benzoyl-5-chlorosulfonyl-3-isobutoxybenzoic acid.

By replacing in Example 6, step D, 5-amino-4-benzoyl-3-ethoxybenzoic acid with 5-amino-4-benzoyl-3-isobutoxybenzoic acid, and following the procedure described, 4-benzoyl-5-chlorosulfonyl-3-isobutoxybenzoic acid is obtained.

EXAMPLE 9

3-Allyloxy-4-benzoyl-5-chlorosulfonylbenzoic acid

A. 3-Allyloxy-4-benzoyl-5-nitrobenzoic acid.

By replacing in Example 6, step B, ethyl iodide with an equimolar amount of allyl bromide, and following the procedure described, 3-allyloxy-4-benzoyl-5-nitrobenzoic acid is obtained with a melting point of 192°–193° C.

B. 3-Allyloxy-5-amino-4-benzoylbenzoic acid.

By replacing in Example 1, step C, 4-benzoyl-3-n-butoxy-5-nitrobenzoic acid with 3-allyloxy-4-benzoyl-5-nitrobenzoic acid, and following the procedure described, 3-allyloxy-5-amino-4-benzoylbenzoic acid is obtained with a melting point of 206.5°–207.5° C.

C. 3-Allyloxy-4-benzoyl-5-chlorosulfonylbenzoic acid.

By replacing in Example 6, step D, 5-amino-4-benzoyl-3-ethoxybenzoic acid with 3-allyloxy-5-amino-4-benzoylbenzoic acid, and following the procedure described, 3-allyloxy-4-benzoyl-5-chlorosulfonylbenzoic acid is obtained.

EXAMPLE 10

4-Benzoyl-5-chlorosulfonyl-3-propargyloxybenzoic acid

A. 4-Benzoyl-5-nitro-3-propargyloxybenzoic acid.

By replacing in Example 6, step B, ethyl iodide with an equimolar amount of propargyl bromide, and following the procedure described, 4-benzoyl-5-nitro-3-propargyloxybenzoic acid is obtained with a melting point of 169°–172° C.

B. 5-Amino-4-benzoyl-3-propargyloxybenzoic acid.

By replacing in Example 1, step C, 4-benzoyl-3-n-butoxy-5-nitrobenzoic acid with 4-benzoyl-5-nitro-3-propargyloxybenzoic acid, and following the procedure described, 5-amino-4-benzoyl-3-propargyloxybenzoic acid is obtained with a melting point of 191.5°–192.5° C.

C. 4-Benzoyl-5-chlorosulfonyl-3-propargyloxybenzoic acid.

By replacing in Example 6, step D, 5-amino-4-benzoyl-3-ethoxybenzoic acid with 5-amino-4-benzoyl-3-propargyloxybenzoic acid, and following the procedure described, 4-benzoyl-5-chlorosulfonyl-3-propargyloxybenzoic acid is obtained.

EXAMPLE 11

4-Benzoyl-3-(p-chlorobenzyloxy)-5-chlorosulfonylbenzoic acid

A. 4-Benzoyl-3-(p-chlorobenzyloxy)-5-nitrobenzoic acid.

By replacing in Example 6, step B, ethyl iodide with an equimolar amount of p-chlorobenzyl chloride, and following the procedure described, 4-benzoyl-3-(p-chlorobenzyloxy)-5-nitrobenzoic acid is obtained with a melting point of 253°–254° C.

B. 5-Amino-4-benzoyl-3-(p-chlorobenzyloxy)benzoic acid.

By replacing in Example 1, step C, 4-benzoyl-3-n-butoxy-5-nitrobenzoic acid with 4-benzoyl-3-(p-chlorobenzyloxy)-5-nitrobenzoic acid, and following the procedure described, 5-amino-4-benzoyl-3-(p-chlorobenzyloxy)benzoic acid is obtained with a melting point of 248°–249° C.

C. 4-Benzoyl-3-(p-chlorobenzyloxy)-5-chlorosulfonylbenzoic acid.

By replacing in Example 6, step D, 5-amino-4-benzoyl-3-ethoxybenzoic acid with 5-amino-4-benzoyl-3-(p-chlorobenzyloxy)-benzoic acid, and following the procedure described, 4-benzoyl-3-(p-chlorobenzyloxy)-5-chlorosulfonylbenzoic acid is obtained.

EXAMPLE 12

4-Benzoyl-5-chlorosulfonyl-3-(2-pyridylmethoxy)benzoic acid

A. 4-Benzoyl-5-nitro-3-(2-pyridylmethoxy)benzoic acid.

By replacing in Example 6, step B, ethyl iodide with an equimolar amount of 2-chloromethylpyridine hydrochloride and using the double amount of sodium, and following the procedure described, 4-benzoyl-5-nitro-3-(2-pyridylmethoxy)benzoic acid is obtained with a melting point of 224°–225° C.

B. 5-Amino-4-benzoyl-3-(2-pyridylmethoxy)benzoic acid.

By replacing in Example 1, step C, 4-benzoyl-3-n-butoxy-5-nitrobenzoic acid with 4-benzoyl-5-nitro-3-(2-pyridylmethoxy)benzoic acid, and following the procedure described, 5-amino-4-benzoyl-3-(2-pyridylmethoxy)benzoic acid is obtained with a melting point of 212°–213° C.

C. 4-Benzoyl-5-chlorosulfonyl-3-(2-pyridylmethoxy)-benzoic acid.

By replacing in Example 1, step D, 5-amino-4-benzoyl-3-n-butoxybenzoic acid with 5-amino-4-benzoyl-3-(2-pyridylmethoxy)benzoic acid, and following the rocedure described, 4-benzoyl-5-chlorosulfonyl-3-(2-pyridylmethoxy)benzoic acid is obtained.

EXAMPLE 13

3-n-Butoxy-5-chlorosulfonyl-4-(4'-methylbenzoyl)-benzoic acid.

A. 3-Hydroxy-4-(4'-methylbenzoyl)-5-nitrobenzoic acid

By replacing in Example 1, step A, 3-amino-4benzoyl-5-nitrobenzoic acid with 3-amino-4-(4'-methylbenzoyl)-5-nitrobenzoic acid and following the procedure described, 3-hydroxy-4-(4'-methylbenzoyl)-5-nitrobenzoic acid is obtained as a hemihydrate with a melting point of 249.5°–251° C.

B. Ethyl 3-hydroxy-4-(4'-methylbenzoyl)-5-nitrobenzoate.

By replacing in Example 6, step A, 4-benzoyl-3hydroxy-5-nitrobenzoic acid with 3-hydroxy-4-(4'-methylbenzoyl)-5-nitrobenzoic acid and following the procedure described, ethyl 3-hydroxy-4-(4'-methylbenzoyl)-5-nitrobenzoate is obtained with a melting point of 145°–147° C.

C. 3-n-Butoxy-4-(4'-methylbenzoyl)-5-nitrobenzoic acid

By replacing in Example 6, step B, ethyl 4-benzoyl3-hydroxy-5-nitrobenzoate and ethyl iodide with equimolar amounts of ethyl 3-hydroxy-4-(4'-methylbenzoyl)-5-nitrobenzoate and n-butyl iodide respectively and following the procedure described, 3-n-butoxy-4-(4'-methylbenzoyl)5-nitrobenzoic acid crystallizing with 0.5mole of ethanol is obtained with a melting point of 162.5°–163° C.

D. 5-Amino-3-n-butoxy-4(4'-methylbenzoyl)benzoic acid.

By replacing in Example 1, step C, 4-benzoyl-3-n-butoxy-5-nitrobenzoic acid with 3-n-butoxy-4-(4'-methylbenzoyl)-5-nitrobenzoic acid and following the procedure described, 5-amino-3-n-butoxy-4-(4'-methylbenzoyl)benzoic acid is obtained with a melting point of 170°–172° C.

E. 3-n-Butoxy-5-chlorosulfonyl-4-(4'-methylbenzoyl)-benzoic acid.

By replacing in Example 6, step D, 5-amino-4-benzoyl-3-ethoxybenzoic acid with 5-amino-3-n-butoxy4-(4'-methylbenzoyl)benzoic acid and following the procedure described, 3-n-butoxy-5-chlorosulfonyl-4-(4'-methylbenzoyl)benzoic acid is obtained.

EXAMPLE 14

3-Benzyloxy-5-chlorosulfonyl-4-(4'-methylbenzoyl)-benzoic acid

A. 3-Benzyloxy-4-(4'-methylbenzoyl)-5-nitrobenzoic acid.

By replacing in Example 6, step B, ethyl 4-benzoyl-3-hydroxy-5-nitrobenzoate and ethyl iodide by equimolar amounts of ethyl 3-hydroxy-4-(4'-methylbenzoyl)-5-nitrobenzoate and benzyl bromide respectively and following the procedure described, 3-benzyloxy-4-(4'-methylbenzoyl)-5-nitrobenzoic acid is obtained with a melting point of 222°–223° C.

B. 5-Amino-3-benzyloxy-4-(4'-methylbenzoyl)benzoic acid.

By replacing in Example 1, step C, 4-benzoyl-3-n-butoxy-5-nitrobenzoic acid with 3-benzyloxy-4-(4'-methylbenzoyl)-5-nitrobenzoic acid and following the procedure described, 5-amino-3-benzyloxy-4-(4'-methylbenzoyl)benzoic acid is obtained with a melting point of 182.5°–184° C.

C. 3-Benzyloxy-5-chlorosulfonyl-4-(4'-methylbenzoyl)-benzoic acid.

By replacing in Example 6, step D, 5-amino-4-benzoyl3-ethoxybenzoic acid with 5-amino-3-benzyloxy-4-(4'-methylbenzoyl)benzoic acid and following the procedure described, 3-benzyloxy-5-chlorosulfonyl-4(4'-methylbenzoyl)benzoic acid is obtained.

EXAMPLE 15

3-n-Butoxy-4-(4'-chlorobenzoyl)-5-chlorosulfonylbenzoic acid

A. 4-)4'-Chlorobenzoyl)-3-hydroxy-5-nitrobenzoic acid.

By replacing in Example 1, step A, 3-amino-4-benzoyl5-nitrobenzoic acid with 3-amino-4-(4'-chlorobenzoyl)-5-nitrobenzoic acid and following the procedure described, 4-(4'-chlorobenzoyl)-3-hydroxy-5-nitrobenzoic acid is obtained as a hemihydrate with a melting point of 266.5°–267.5° C.

B. Ethyl 4-(4'-chlorobenzoyl)-3-hydroxy-5-nitrobenzoate.

By replacing in Example 6, step A, 4-benzoyl-3-hydroxy5-nitrobenzoic acid with 4-(4'-chlorobenzoyl)-3-hydroxy-5-nitrobenzoic acid and following the procedure described, ethyl 4-(4'-chlorobenzoyl)-3-hydroxy-5-nitrobenzoate is obtained with a melting point of 188°–191.5° C.

C. 3-n-Butoxy-4-(4'-chlorobenzoyl)-5-nitrobenzoic acid.

By replacing in Example 6, step B, ethyl 4-benzoyl-3-hydroxy-5-nitrobenzoate and ethyl iodide with equimolar amounts of ethyl 4-(4'-chlorobenzoyl)-3-hydroxy-5-nitrobenzoate and n-butyl iodide respectively and following the procedure described, 3-n-butoxy-4-(4'-chlorobenzoyl)-5-nitrobenzoic acid is obtained with a melting point of 180°–182° C.

D. 5-Amino-3-n-butoxy-4-(4'-chlorobenzoyl)benzoic acid

By replacing in Example 1, step C, 4benzoyl-3-n-butoxy-5-nitrobenzoic acid with 3-n-butoxy-4-(4'-chlorobenzoyl)-5-nitrobenzoic acid and following the procedure described, 5-amino-3-n-butoxy-4-(4'-chlorobenzoyl)benzoic acid is obtained with a melting point of 286°–287.5° C.

E. 3-n-Butoxy-4-(4'-chlorobenzoyl)-5-chlorosulfonylbenzoic acid.

By replacing in Example 6, step D, 5-amino-4-benzoyl-3-ethoxybenzoic acid with 5-amino-4-(4'-chlorobenzoyl)-3-n-butoxybenzoic acid and following the procedure described, 3-n-butoxy-4-(4'-chlorobenzoyl)-5-chlorosulfonylbenzoic acid is obtained.

EXAMPLE 16

3-Benzyloxy-4-(4'-chlorobenzoyl)-5-chlorosulfonylbenzoic acid.

A. 3-Benzyloxy-4-(4'-chlorobenzoyl)-5-nitrobenzoic acid.

By replacing in Example 6, step B, ethyl 4-benzoyl-3-hydroxy-5-nitrobenzoate and ethyl iodide with equimolar amounts of ethyl 4-(4'-chlorobenzoyl)-3-hydroxy-5-nitrobenzoate and benzyl bromide respectively and following the procedure described, 3-benzyloxy-4-(4'-chlorobenzoyl)-5-nitrobenzoic acid is obtained with a melting point of 137°–138.5° C.

B. 5-Amino-3-benzyloxy-4-(4'-chlorobenzoyl)benzoic acid.

By replacing in Example 1, step C, 4-benzoyl-3-n-butoxy-5-nitrobenzoic acid with 3-benzyloxy-4-(4'-chlorobenzoyl)-5-nitrobenzoic acid and following the procedure described, 5-amino-3-benzyloxy-4-(4'-chlorobenzoyl)benzoic acid is obtained with a melting point of 196°–197° C.

C. 3-Benzyloxy-4-(4'-chlorobenzoyl)-5-chlorosulfonylbenzoic acid.

By replacing in Example 6, step D, 5-amino-4-benzoyl3-ethoxybenzoic acid with 5-amino-3-benzyloxy-4-(4'-chlorobenzoyl)benzoic acid and following the procedure described, 3-benzyloxy-4-(4'-chlorobenzoyl)-5-chlorosulfonylbenzoic acid is obtained.

EXAMPLE 17

4-Benzoyl-5-chlorosulfonyl-3-methylthiobenzoic acid

A. 2-Benzoyl-5-carboxy-3-nitrobenzenediazonium tetrafluoroborate.

A mixture of 3-amino-4-benzoyl-5-nitrobenzoic acid (57.2 g) and conc. hydrochloric acid (250 ml) is heated on a steam bath for 10 minutes. After cooling, the amine is diazotized by the dropwise addition of a solution of sodium nitrite (16 g) in water (80 ml), while stirring at −5° C to 0° C. After additional stirring at this temperature for 10 minutes, 50% aqueous hydrofluoboric acid (220 ml) is added during about 5 minutes. The mixture is left for 1 hour, keeping the temperature below 0° C by external cooling. The precipitate formed is then collected by filtration and washed with two portions of icecold water (each portion 25 ml). The material is suspended in acetone (200 ml) and stirred for 15 minutes. It is collected by filtration, washed with acetone, followed by diethyl ether and dried to give 2-benzoyl-5-carboxy-3-nitrobenzenediazonium tetrafluoroborate.

B. Ethylxanthic acid 2-benzoyl-5-carboxy-3-nitrophenyl ester.

2-Benzoyl-5-carboxy-3-nitrobenzenediazonium tetrafluoroborate (60 g) is added in portions to a solution of potassium ethyl xanthate (30 g) in water (600 ml) while stirring at 75°–78° C. After additional stirring at this temperature for 30 minutes, the mixture is cooled, and the separated ethylxanthic acid 2-benzoyl-5-carboxy-3-nitrophenyl ester is collected by filtration, washed with water, and dried.

C. 4-Benzoyl-3-methylthio-5-nitrobenzoic acid.

A mixture of ethylxanthic acid 2-benzoyl-5-carboxy-3-nitrophenyl ester (11.7 g), dry ethylene diamine (25 ml), methyl iodide (10 ml) and dry ethanol (50 ml) is stirred at room temperature for 20 hours in a nitrogene atmosphere. The mixture is then poured into a mixture of conc. hydrochloric acid (100 ml) and ice (about 100 g). The resulting precipitate is collected by filtration and washed with water. After drying and recrystallization from isopropanol, 4-benzoyl-3-methylthio-5-nitrobenzoic acid is obtained with a melting point of 210°–213° C.

D. 5-Amino-4-benzoyl-3-methylthiobenzoic acid.

By replacing in Example 1, step C, 4-benzoyl-3-n-butoxy-5-nitrobenzoic acid with 4-benzoyl-3-methylthio-5-nitrobenzoic acid and following the procedure described, 5-amino-4-benzoyl-3-methylthiobenzoic acid is obtained with a melting point of 158.5°–159° C.

E. 4-Benzoyl-5-chlorosulfonyl-3-methylthiobenzoic acid.

By replacing in Example 6, step D, 5-amino-4-benzoyl-3-ethoxybenzoic acid with 5-amino-4-benzoyl-3-methylthiobenzoic acid and following the procedure described, 4-benzoyl-5-chlorosulfonyl-3-methylthiobenzoic acid is obtained.

EXAMPLE 18

4-Benzoyl-3-benzylthio-5-chlorosulfonylbenzoic acid

A. 4-Benzoyl-5-nitro-3-thiocyanobenzoic acid.

To a mixture of potassium thiocyanate (42 g), copper thiocyanate (4s g) and water (400 ml), 2-benzoyl-5-carboxy3-nitrobenzenediazonium tetrafluoroborate (prepared as described in Example 17, step A; 28 g) is added in portions while stirring at 45°–50° C. After the addition is completed, the mixture is stirred at about 50° C. for a further 4 hours and thereafter at room temperature for about 20 hours. The resulting precipitate is collected by filtration, washed with water and dried. The dried solids are then extracted with boiling ethanol (three portions of 250 ml, 100 ml, and 100 ml, respectively) and filtered hot. The combined filtrates are evaporated in vacuo and the residue is crystallized by trituration with 50% aqueous ethanol (100 ml). The material is collected by filtration, washed with cold 50% ethanol and dried. After recrystallization from aqueous ethanol, 4-benzoyl-5-nitro-3-thiocyanobenzoic acid is obtained with a melting point of 183.5°–184.5° C.

B. 2,2'-Dibenzoyl-3,3'-dibenzylthio-5,5'-dicarboxyazobenzene.

To a hot solution of 4-benzoyl-5-nitro-3-thiocyanobenzoic acid (6.65 g) in 2 N sodium hydroxide (65 ml), glucose (5.0 g) is added and the solution is heated on a steam bath for 15 minutes. After cooling to about 50° C., benzyl bromide (3.5 ml) is added; the mixture is stirred at room temperature for 2–3 hours and is then left in a refrigerator for about 20 hours. The precipitated material is collected by filtration and is washed with cold 2 N sodium hydroxide. After drying, the material is dissolved in hot water (about 100 ml) and concentrated hydrochloric acid (5 ml) is added. The resulting precipitate is, after cooling, collected by filtration and washed with water. After drying and recrystallization from ethanol, 2,2'-dibenzoyl-3,3'-dibenzylthio-5,5'-dicarboxyazobenzene is obtained with a melting point of 218°–219.5° C.

C. 5-Amino-4-benzoyl-3-benzylthiobenzoic acid.

To a solution of stannous chloride dihydrate (6.0 g) in a mixture of acetic acid (40 ml) and concentrated hydrochloric acid (12 ml), 2,2'-dibenzoyl-3,3'-dibenzylthio5,5'-dicarboxyazobenzene (3.0 g) is added, and the mixture is stirred at 100°–110° C. for about 3 hours. The resulting solution is then evaporated in vacuo, and the residue is triturated with water (about 100 ml). The resulting precipitate is collected by filtration and washed with water. After drying and recrystallization from aqueous ethanol, 5-amino-4-benzoyl-3-benzylthiobenzoic acid is obtained with a melting point of 141°–142° C.

D. 4-Benzoyl-3-benzylthio-5-chlorosulfonylbenzoic acid.

By replacing in Example 6, step D, 5-amino-4-benzoyl-3-ehtoxybenzoic acid with 5-amino-4-benzoyl-3-benzylthiobenzoic acid and following the procedure described, 4-benzoyl-3-benzylthio-5-chlorosulfonylbenzoic acid is obtained with a melting point of 182°–184° C.(dec)

EXAMPLE 19

4-Benzoyl-5-chlorosulfonyl-3-n-propylthiobenzoic acid.

A. 2,2'-Dibenzoyl-5,5'-dicarboxy-3,3'-di-(n-propylthio)-azobenzene.

By replacing in Example 18, step B, benzyl bromide with an equimolar amount of n-propyl iodide and performing the reaction at 55°–60° C., 2,2'-dibenzoyl-5,5'-dicarboxy-3,3'-di-(n-propylthio)azobenene is obtained with a melting point of 164°–165° C.

B. 5-Amino-4-benzoyl-3-n-propylthiobenzoic acid.

By replacing in Example 18, step C, 2,2'-dibenzoyl3-,3'-dibenzylthio-5,5'-dicarboxyazobenzene with 2,2'-dibenzoyl-5,5'-dicarboxy-3,3'-di-(n-propylthio)azobenzene and following the procedure described, 5-amino-4-benzoyl-3-n-propylthiobenzoic acid is obtained with a melting point of 124.5°–125.5° C.

C. 4-Benzoyl-5-chlorosulfonyl-3-n-proplythiobenzoic acid.

By replacing in Example 6, step D, 5-amino-4-benzoyl-3-ethoxybenzoic acid with 5-amino-4-benzoyl-3-n-propylthiobenzoic acid and following the procedure described, 4-benzoyl-5-chlorosulfonyl-3-n-propylthiobenzoic acid is obtained.

EXAMPLE 20

4-benzoyl3-n-butylthio-5-chlorosulfonylbenzoic acid

A. 2,2'-Dibenzoyl-3,3'-di-(n-butylthio)-5,5'-dicarboxyazobenzene.

By replacing in Example 18, step B, benzyl bromide with an equimolar amount of n-butyl iodide and performing the reaction at 55°–60° C., 2,2'-dibenzoyl-3,3'-di-(n-butylthio)-5,5'-dicarboxyazobenzene is obtained with a melting point of 102°–103° C.

B. 5-Amino-4-benzoyl-3-n-butylthiobenzoic acid.

By replacing in Example 18, step C, 2,2'-dibenzoyl-3,3'-dibenzylthio-5,5'-dicarboxyazobenzene with 2,2'-di-benzoyl-3,3'-di-(n-butylthio)-5,5'-dicarboxyazobenzene and following the procedure described, 5-amino-4-benzoyl-3-n-butylthiobenzoic acid is obtained with a melting point of 144°–145° C.

C. 4-Benzoyl-3-n-butylthio-5-chlorosulfonylbenzoic acid.

By replacing in Example 6, step D, 5-amino-4-benzoyl-3-ethoxybenzoic acid with 5-amino-4-benzoyl-3-n-butylthiobenzoic acid and following the procedure described, 4-benzoyl-3-n-butylthio-5-chlorosulfonylbenzoic acid is obtained.

EXAMPLE 21

4-Benzoyl-5-chlorosulfonyl-3-isopentylthiobenzoic acid

A. 2,2'-Dibenzoyl-5,5'-dicarboxy-3,3'-diisopentylthioazobenzene.

By replacing in Example 18, step B, benzyl bromide with an equimolar amount of isopentyl iodide and performing the reaction at 55°–60° C., 2,2'-dibenzoyl-5,5'-dicarboxy-3,3'-diisopentylthioazobenzene is obtained with a melting point of 143°–144° C.

B. 5-Amino-4-benzoyl-3-isopentylthiobenzoic acid.

By replacing in Example 18, step C, 2,2'-dibenzoyl-3,3'-dibenzylthio-5,5'-dicarboxyazobenzene with 2,2'-di-benzoyl-5,5'-dicarboxy-3,3'-diisopentylthioazobenzene and following the procedure described, 5-amino-4-benzoyl-3-isopentylthiobenzoic acid is obtained with a melting point of 141°–142° C.

C. 4-Benzoyl-5-chlorosulfonyl-3-isopentylthiobenzoic acid.

By replacing in Example 6, step D, 5-amino-4-benzoyl-3-ethoxybenzoic acid with 5-amino-4-benzoyl-3-isopentylthiobenzoic acid and following the procedure described, 4-benzoyl-5-chlorosulfonyl-3-isopentylthiobenzoic acid is obtained.

EXAMPLE 22

3-Allylthio-4-benzoyl-5-chlorosulfonylbenzoic acid.

A. 3,3'-Diallylthio-2,2'-dibenzoyl-5,5'-dicarboxyazobenzene.

By replacing in Example 18, step B, benzyl bromide with an equimolar amount of allyl bromide and following the procedure described, 3,3'-diallylthio-2,2'-dibenzoyl-5,5'-dicarboxyazobenzene is obtained with a melting point of 161.5°–163° C.

B. 3-Allylthio-5-amino-4-benzoylbenzoic acid.

By replacing in Example 18, step C, 2,2'-dibenzoyl-3,3'-dibenzylthio-5,5'-dicarboxyazobenzene with 3,3'-diallylthio-2,2'-dibenzoyl-5,5'-dicarboxyazobenzene and following the procedure described, 3-allylthio-5-amino-4-benzoylbenzoic acid is obtained with a melting point of 152.5°–153.5° C.

C. 3-Allylthio-4-benzoyl-5-chlorosulfonylbenzoic acid.

By replacing in Example 6, step D, 5-amino4-benzoyl-3-ethoxybenzoic acid with 3-ellylthio-5-amino-4-benzoylbenzoic acid and following the procedure described, 3-allylthio-4-benzoyl-5-chlorosulfonylbenzoic acid is obtained.

EXAMPLE 23

4-Benzoyl-5-chlorosulfonyl-3-(2-phenethyl)benzoic acid.

A. 2-Benzoyl-5-carboxy-3-nitrobenzenediazonium chloride.

To a stirred, hot solution of 3-amino-4-benzoyl-5-nitrobenzoic acid (11.4g) in acetic acid (55 ml), conc. hydrochloric acid (60 ml) is added dropwise. The mixture is vigorously stirred at 70°–80° C. for a further 20 minutes to precipitate the aminehydrochloride. Conc. hydrochloric acid (30 ml) is added, at about 50° C. and, after cooling, the amine is diazotized by the dropwise addition of a solution of sodium nitrite (3.1 g) in water (12 ml) while sitrring at 0°–5° C. After additional sitrring at this temperature for 30 minutes, the precipitated 2-benzoyl-5-carboxy-3-nitrobenzenediazonium chloride is collected by filtration and washed with ice-cold water followed by acetone and water. The diazonium-salt is used moist in the next step.

B. 4-Benzoyl-5-nitro-3-styrylbenzoic acid.

To a solution of cinnamic acid (3.1 g) in acetonitrile (200 ml), moist 2-benzoyl-5-carboxy-3-nitrobenzenediazonium chloride (corresponding to about 8 g dry material) is added. To the vigorously stirred suspension, a solution of sodium acetate trihydrate (9.4 g) in water (160 ml) is added, followed immediately by a solution of cupric chloride dihydrate (1 g) in water (10 ml). After stirring at room temperature for a further 2 hours, the vigorous nitrogen-evolution has subsided and the mixture is diluted with water (180 ml) followed by diethyl ether (130 ml). The mixture is filtered, and the organic layer is separated. The aqueous layer is extracted with five portions of diethyl ether, and the combined ether extracts are washed with water and evaporated in vacuo. The residue is crystallized by trituration with aqueous ethanol (50–100 ml). The crude 4-benzoyl-5-nitro-3-styrylbenzoic acid obtained is collected by filtration, washed with aqueous ethanol and dried. The crude acid is dissolved in hot 1 N sodium hydrogen carbonate, and after cooling, the precipitated sodium 4-benzoyl-5-nitro-3-styrylbenzoate is collected by filtration and washed with a small amount of icecold water. After drying, the salt is dissolved in hot water (100 ml) and the solution is clairied by filtration hot in the presence of decolorizing carbon. 4-Benzoyl-5-nitro-3-styrylbenzoic acid is precipitated by acidification with acetic acid. It is collected by filtration and is, after drying, obtained with a melting point of 288°–289° C. (dec.).

C. 2,2'-Benzoyl-5,5'-carboxy-3,3'-di(2-phenethyl)azobenzene.

A suspension of 4-benzoyl-5-nitro-3-styrylbenzoic acid (3.7 g) in ethanol (200 ml) is hydrogenated in the presence of palladium-on-carbon catalyst (10%; 0.35 g). After the theoretical amount of hydrogen has been absorbed, the catalyst is removed by filtration, and the 2,2'-dibenzoyl-5,5'-dicarboxy-3,3'-di(2-phenethyl)azobenzene is precipitated from the filtrate by dilution with water. The compound is collected by filtration and is, after drying and recrystallization from aqueous ethanol, obtained with a melting point of 170°–172° C. (dec.).

D. 5-Amino-4-benzoyl-3-(2-phenethyl)benzoic acid.

By replacing in Example 18, step C, 2,2'-dibenzoyl-3,3'-dibenzylthio-5,5'-dicarboxyazobenzene with 2,2'-di-benzoyl-5,5'-dicarboxy-3,3'-di(2-phenethyl)azobenzene and following the procedure described, 5-amino-4-benzoyl-3-(2-phenethyl)benzoic acid is obtained with a melting point of 150°–152.5° C.

E. 4-Benzoyl-5-chlorosulfonyl-3-(2-phenethyl)benzoic acid.

By replacing in Example 6, step D, 5-amino-4-benzoyl-3-ethoxybenzoic acid with 5-amino-4-benzoyl-3-(2-phenethyl) benzoic acid and following the procedure described, 4-benzoyl-5-chlorosulfonyl-3-(2-phenethyl)benzoic acid is obtained.

EXAMPLE 24

4-Benzyl-3-benzyloxy-5-chlorosulfonylbenzoic acid

A. 5-Amino-4-benzyl-3-benzyloxybenzoic acid.

A mixture of 4-benzoyl-3-benzyloxy-5-nitrobenzoic acid (2.7 g), 98% aqueous hydrazine hydrate (4.5 ml), potassium hydroxide (1.5 g) in water (3.0 ml) and di-ethylene glycol (20 ml) is stirred at about 130° C. for 1 hour. The temperature is then slowly raised to 215° C. allowing volatile material to distil off. The stirring at 215° C. is continued for a further 2–3 hours until the nitrogen evolution has ceased. After cooling and dilution with water (30 ml), the resulting solution is acidified with conc. hydrochloric acid (3 ml). The resulting precipitate is collected by filtration and washed with water. After drying and recrystallization twice from 96% ethanol, 5-amino-4-benzyl-3-benzyloxybenzoic acid is obtained with a melting point of 207.5°–209.5° C.

B. 4-Benzyl-3-benzyloxy-5-chlorosulfonylbenzoic acid.

By replacing in Example 1, step D, 5-amino-4-benzoyl-3-n-butoxybenzoic acid with 5-amino-4-benzyl-3-benzoyloxybenzoic acid and following the procedure described, 4-benzyl-3-benzyloxy-5-chlorosulfonylbenzoic acid is obtained with a melting point of 164°–166° C.

EXAMPLE 25

4-Benzyl-5-chlorosulfonyl-3-ethoxybenzoic acid

A. 5-Amino-4-benzyl-3-ethoxybenzoic acid.

By replacing in Example 24, step A, 4-benzoyl-3-benzyloxy-5-nitrobenzoic acid with 4-benzoyl-3-ethoxy-5-nitrobenzoic acid and following the procedure described, 5-amino-4-benzyl-3-ethoxybenzoic acid is obtained with a melting point of 165°–167° C.

B. 4-Benzyl-5-chlorosulfonyl-3-ethoxybenzoic acid.

By replacing in Example 6, step D, 5-amino-4-benzoyl-3-ethoxybenzoic acid with 5-amino-4-benzyl-3-ethoxybenzoic acid and following the procedure described, 4-benzyl-5-chlorosulfonyl 3-ethoxybenzoic acid is obtained.

EXAMPLE 26

4-Benzyl-5-chlorosulfonyl-3-n-propoxybenzoic acid

A. 5-Amino4-benzyl-3-n-propoxybenzoic acid.

By replacing in Example 24, step A, 4-benzoyl-3-benzyloxy-5-nitrobenzoic acid with 5-amino-4-benzoyl-3-n-propoxybenzoic acid and following the procedure described, 5-amino-4-benzyl-3-n-propoxybenzoic acid is obtained with a melting point of 161°–162° C.

B. 4-Benzyl-5-chlorosulfonyl-3-n-propoxybenzoic acid.

By replacing in Example 6, step D, 5-amino-4-benzoyl-3-ethoxybenzoic acid with 5-amino-4-benzyl-3-n-propoxybenzoic acid and following the procedure described, 4-benzyl-5-chlorosulfonyl-3-n-propoxybenzoic acid is obtained.

EXAMPLE 27

4-Benzyl-3-(p-chlorobenzyloxy)-5-chlorosulfonylbenzoic acid.

A. 5-Amino-4-benzyl-3-(p-chlorobenzyloxy)benzoic acid.

By replacing in Example 24, step A, 4-benzoyl3-benzyloxy-5-nitrobenzoic acid with 5-amino-4-benzoyl-3-(p-chlorobenzyloxy)benzoic acid and following the procedure described, 5-amino-4-benzyl-3-(p-chlorobenzyloxy)benzoic acid is obtained with a melting point of 199°–200° C.

B. 4-Benzyl-3-(p-chlorobenzyloxy)-5-chlorosulfonylbenzoic acid.

By replacing in Example 6, step D, 5-amino4-benzoyl-3-ethoxybenzoic acid with 5-amino-4-benzyl-3-(p-chlorobenzyloxy)benzoic acid and following the procedure described, 4-benzyl-3-(p-chlorobenzyloxy)-5-chlorosulfonylbenzoic acid is obtained.

EXAMPLE 28

4-Benzyl-5-chlorosulfonyl-3-methylthiobenzoic acid

A. 5-Amino4-benzyl-3-methylthiobenzoic acid.

By replacing in Example 24, step A, 4-benzoyl-3-benzyloxy-5-nitrobenzoic acid with 4-benzoyl-3-methylthio-5-nitrobenzoic acid and following the procedure described, 5-amino-4-benzyl-3-methylthiobenzoic acid is obtained with a melting point of 153°–154° C.

B. 4-Benzyl-5-chlorosulfonyl-3-methylthiobenzoic acid

By replacing in Example 6, step D, 5-amino-4-benzoyl-3-ethoxybenzoic acid with 5-amino-4-benzyl-3-methylthiobenzoic acid and following the procedure described, 4-benzyl-5-chlorosulfonyl-3-methylthiobenzoic acid is obtained.

EXAMPLE 29

4-Benzyl-5-chlorosulfonyl-3-n-propylthiobenzoic acid

A. 5-Amino-4-benzyl-3-n-propylthiobenzoic acid.

By replacing in Example 24, step A, 4-benzoyl-3-benzyloxy-5-nitrobenzoic acid with 2,2'-dibenzoyl-5,5'-dicarboxy-3,3'-di-(n-propylthio)azobenzene and following the procedure described, 5-amino-4-benzyl-3-n-propylthiobenzoic acid is obtained with a melting point of 151°–152° C.

B. 4-Benzyl-5-chlorosulfonyl-3-n-propylthiobenzoic acid

By replacing in Example 6, step D, 5-amino-4-benzoyl-3-ethoxybenzoic acid with 5-amino-4-benzyl-3-n-propylthiobenzoic acid and following the procedure described, 4-benzyl-5-chlorosulfonyl-3-n-propylthiobenzoic acid is obtained.

EXAMPLE 30

4-Benzyl-3-n-butylthio-5-chlorosulfonylbenzoic acid

A. 5-Amino-4-benzyl-3-n-butylthiobenzoic acid

By replacing in Example 24, step A, 4-benzoyl-3-benzyloxy-5-nitrobenzoic acid with 2,2'-dibenzoyl-3,3'-di-(n-butylthio)-5,5'-dicarboxyazobenzene and following the procedure described, 5-amino-4-benzyl-3-n-butylthiobenzoic acid is obtained with a melting point of 136°–138° C.

B. 4-Benzyl-3-n-butylthio-5-chlorosulfonylbenzoic acid

By replacing in Example 6, step D, 5-amino-4-benzoyl-3-ethoxybenzoic acid with 5-amino-4-benzyl-3-n-butylthiobenzoic acid and following the procedure described, 4-benzyl-3-n-butylthio-5-chlorosulfonylbenzoic acid is obtained.

EXAMPLE 31

4-Benzyl-3-benzylthio-5-chlorosulfonylbenzoic acid

A. 5-Amino-4-benzyl-3-benzylthiobenzoic acid

By replacing in Example 24, step A, 4-benzoyl-3-benzyloxy-5-nitrobenzoic acid with 5-amino-4-benzoyl-3-benzylthiobenzoic acid and following the procedure described, 5-amino-4-benzyl-3-benzylthiobenzoic acid is obtained with a melting point of 256°–257° C.

B. 4-Benzyl-3-benzylthio-5-chlorosulfonylbenzoic acid

By replacing in Example 6, step D, 5-amino-4-benzoyl-3-ethoxybenzoic acid with 5-amino-4-benzyl-3-benzylthiobenzoic acid and following the procedure described, 4-benzyl-3-benzylthio-5-chlorosulfonylbenzoic acid is obtained.

EXAMPLE 32

4-Benzoyl-3-n-butoxy-5-sulfamylbenzoic acid.

4-Benzoyl-3-n-butoxy-5-chlorosulfonylbenzoic acid (1.5 g) is in portions added to conc. ammonium hydroxide (15 ml) while stirring at 10°–12° C. After additional stirring at room temperature for 16 hours, the mixture is left in a refrigerator for 4–5 hours. The separated ammonium salt is collected by filtration and washed with a small amount of icecold water. After drying, the salt is dissolved in 1 N sodium hydroxide (15 ml) and the solution is dropwise added to icecold 1 N acetic acid (20 ml) while stirring. The separated material is collected by filtration, washed with water and dried in the air. The product is recrystallized from aqueous ethanol, and the thus purified material is dissolved in 1 N NaOH (15 ml). The solution is dropwise added to icecold 1 N acetic acid (18 ml) while stirring. The precipitated material is collected by filtration, washed with water and dried in vacuo in the presence of $P_2O_5$, to give 4-benzoyl-3-n-butoxy-5-sulfamylbenzoic acid.

EXAMPLES 33–50

By following the procedure described in Example 32 but replacing the 4-benzoyl-3-n-butoxy-5-chlorosulfonylbenzoic acid with other 3-substituted 4-benzoyl-5-chlorosulfonylbenzoic acids described in Examples 2–12 and 17–23, the 3-substituent of which are as defined in Table I below, the corresponding 3-substituted 4-benzoyl-5-sulfamylbenzoic acids of Table I are obtained.

Table I.

| Ex. No. | 3-substituent |
|---|---|
| 33 | ethoxy |
| 34 | n-propoxy |
| 35 | n-pentyloxy |
| 36 | n-hexyloxy |
| 37 | isobutoxy |
| 38 | allyloxy |
| 39 | propargyloxy |
| 40 | benzyloxy |
| 41 | p-chlorobenzyloxy |
| 42 | 2-phenethoxy |
| 43 | 2-pyridylmethoxy |
| 44 | methylthio |
| 45 | benzylthio |
| 46 | n-propylthio |
| 47 | n-butylthio |
| 48 | isopentylthio |
| 49 | allylthio |
| 50 | 2-phenethyl |

The compound prepared as in Examples 33, 36, and 39 are obtained as crystals containing 1.5 moles of water, 1 mole of water, and 1 mole of ethanol, respectively.

EXAMPLES 51–68

After heating of the 3-$YR_1$-4-benzoyl-5-sulfamylbenzoic acids described in Examples 32–46 and 48–50 for about 10 minutes to the temperatures defined in Table II below, the corresponding 4-$YR_1$-6-carboxy-3-phenyl-1,2-benzisothiazole 1,1-dioxides of Table II are obtained.

Table II

| Ex. No. | Temperature ° C. of dehydration | 4-substituent | M.p. ° C. of 4-$YR_1$-6-carboxy-3-phenyl-1,2-benzisothiazole-1,1-dioxides |
|---|---|---|---|
| 51 | 175–180 | n-butoxy | 209–211 |
| 52 | 225–230 | ethoxy | 238–240 |
| 53 | 180–185 | n-propoxy | 215–216 |
| 54 | 165–170 | n-pentyloxy | 180–181 |
| 55 | 165–170 | n-hexyloxy | 233–234 |
| 56 | 155–160 | isobutoxy | 199–201 |
| 57 | 200–205 | allyloxy | 209–210 |
| 58 | 150–155 | propargyloxy | 213–214.5 |
| 59 | 205–210 | benzyloxy | 229–231 |
| 60 | 195–200 | p-chlorobenzyloxy | 215–216 |
| 61 | 175–180 | 2-phenethoxy | 208–210 |
| 62 | 275–280 | 2-pyridylmethoxy | 277–278 |
| 63 | 185–190 | methylthio | 247–249 |
| 64 | 175–180 | benzylthio | 150–152 |
| 65 | 160–165 | n-propylthio | 181–183 |
| 66 | 170–175 | isopentylthio | 160–162 |
| 67 | 140–145 | allylthio | 195–197 |
| 68 | 200–205 | 2-phenethyl | 169–172 |

Example 69

4-Benzoyl-3-n-butoxy-5-sulfamylbenzoic acid 4-n-Butoxy-6-carboxy-3-phenyl-1,2-benzisothiazole, 1,1-dioxide (1.0 g) is dissolved in 1 N sodium hydroxide (10 ml) and the resulting solution is added to icecold 1 N acetic acid (12 ml), while stirring. The resulting precipitate is collected by filtration and washed with water. After drying in vacuo in the presence of $P_2O_5$, 4-benzoyl-3-n-butoxy-5-sulfamylbenzoic acid is obtained. The material is identical (IR, analysis) with the material prepared as in Example 32.

EXAMPLES 70–73

By following the procedure of Example 32, but replacing the 4-benzoyl-3-n-butoxy-5-chlorosulfonylbenzoic acid with 3-$YR_1$-4-$R_2CO$-5-chlorosulfonylbenzoic acid as defined in the Table below, the corresponding 3-$YR_1$-4-$R_2CO$-5-sulfamylbenzoic acids are obtained.

Table III

| Ex. No. | 3-substituent | 4-substituent |
|---|---|---|
| 70 | n-butoxy | 4'-methylbenzoyl |
| 71 | benzyloxy | 4'-methylbenzoyl |
| 72 | n-butoxy | 4'-chlorobenzoyl |
| 73 | benzyloxy | 4'-chlorobenzoyl |

EXAMPLES 74–75

After heating of the 3-substituted-4-(4'-methylbenzoyl)-5-sulfamylbenzoic acids of Examples 70–71 for 10 minutes to 165°–170° C. and 180°–185° C. respectively, 4-n-butoxy-6-carboxy-3-(4'-methylphenyl)-1,2-benzisothiazole 1,1-dioxide and 4-benzyloxy-6-carboxy-3-(4'-methylphenyl)-1,2-benzisothiazole 1,1-dioxide are obtained with melting points of 194°–196° C. and 220°–221° C. respectively.

EXAMPLES 76–77

After heating of the 3-substituted 4-(4'-chlorobenzoyl)-5-sulfamylbenzoic acids of Examples 72–73 for 10 minutes to 190°–195° C. and 215°–220° C. respectively, 4-n-butoxy-6-carboxy-3-(4'-chlorophenyl)-1,2-benzisothiazole 1,1-dioxide and 4-benzyloxy-6-carboxy-3-(4'-chlorophenyl)-1,2-benzisothiazole 1,1- dioxide are obtained with melting points of 208°–210° C. and 229°–231° C. respectively.

EXAMPLE 78

4-Benzyl-3-benzyloxy-5-sulfamylbenzoic acid

4-Benzyl-3-benzyloxy-5-chlorosulfonylbenzoic acid (1.0 g) is in portions added to conc. ammonium hydroxide (10 ml) while stirring at 10°–12° C. After additional stirring at room temperature for about 20 hours, the mixture is left in a refrigerator for 4–5 hours. The separated ammonium salt is then collected by filtration and washed with a small amount of ice-cold water. After drying, the salt is dissolved in hot water (20 ml), and the solution is clarified by filtration hot in the presence of decolorizing carbon. The solution is then acidified with 4 N HCl (2.0 ml) and, after cooling, the resulting precipitate is collected by filtration, washed with water and dried. After recrystallization twice from ethanol, 4-benzyl-3-benzyloxy-5-sulfamylbenzoic acid is obtained with a melting point of 249.5°–251° C.

EXAMPLES 79–85

By following the procedure described in Example 78, but replacing the 4-benzyl-3-benzyloxy-5-chlorosulfonylbenzoic acid with other 3-substituted 4-benzyl-5-chlorosulfonylbenzoic acids described in Examples 25–31, the 3-substituent of which are as defined in Table IV below, the corresponding 3-substituted 4-benzyl-5-sulfamylbenzoic acids of Table IV are obtained.

Table IV

| Ex. No. | 3-substituent | M.p. °C. of 3-sunstituted 4-benzyl-5-sulfamylbenzoic acids. |
|---|---|---|
| 79 | ethoxy | 235–236 |
| 80 | n-propoxy | 230–232.5 |
| 81 | p-chlorobenzyloxy | 235–237 |
| 82*) | methylthio | 233–234 |
| 83 | n-propylthio | 205–206 |
| 84 | n-butylthio | 205–205.5 |
| 85 | benzylthio | 222–224 |

*)The compound of Example 82 is obtained as a hemihydrate.

EXAMPLE 86

4-Benzyl-3-n-butoxy-5-sulfamylbenzoic acid

A mixture of 4-benzoyl-3-n-butoxy-5-sulfamylbenzoic acid (0.94 g), 98% aqueous hydrazine hydrate (1.5 ml), potassium hydroxide (0.5 g) in water (1.0 ml) and diethylene glycol (6.5 ml) is stirred at about 130° C. for 3 hours. The temperature is then slowly raised to 215° C. allowing volatile material to distil off. The stirring at 215° C. is continued for a further 2–3 hours until the nitrogen evolution has ceased. After cooling and dilution with water (10 ml), the resulting solution is acidified with conc. hydrochloric acid (1 ml). The resulting precipitate is collected by filtration and washed with water. After drying and recrystallization twice from aqueous ethanol, 4-benzyl-3-n-butoxy-5-sulfamylbenzoic acid is obtained with a melting point of 228°–229° C.

EXAMPLES 87–95

By following the procedure described in Example 86, but replacing the 4-benzoyl-3-n-butoxy-5-sulfamylbenzoic acid with other 3-substituted 4-benzoyl-5-sulfamylbenzoic acids, described in Examples 34–38, 40, 47–48 and 50, the 3-substituents of which are as defined in Table V below, the corresponding 3-substituted 4-benzyl-5-sulfamylbenzoic acids of Table V are obtained.

Table V

| Ex. No. | 3-substituent | M.p. °C. of 3-substituted 4-benzyl-5-sulfamylbenzoic acids |
|---|---|---|
| 87 | n-propoxy | 230–232.5 |
| 88 | n-pentyloxy | 223.5–224.5 |
| 89 | n-hexyloxy | 213.5–214.5 |
| 90 | isobutoxy | 218–220 |
| 91 | allyloxy | 238–240 |
| 92 | benzyloxy | 249.5–251 |
| 93 | n-butylthio | 205–205.5 |
| 94 | isopentylthio | 203–205 |
| 95 | 2-phenethyl | 206–208 |

The compounds prepared as in Examples 87 and 93 are identical (IR, analysis) with those of Examples 80 and 84 respectively.

EXAMPLES 96–99

By following the procedure of Example 86, but replacing 4-benzoyl-3-n-butoxy-5-sulfamylbenzoic acid with 3-$YR_1$-4-$R_2$CO-5-sulfamylbenzoic acids as defined in the Table VI the corresponding 3-$YR_1$-4-$R_2CH_2$-5-sulfamylbenzoic acids are obtained:

Table VI

| Ex. No. | 3-substituent | 4-substituent | M.p. °C. of 3-$YR_1$-4-$R_2CH_2$-5-sulfamylbenzoic acids |
|---|---|---|---|
| 96 | n-butoxy | 4'-methylbenzyl | 228.5–229 |
| 97 | benzyloxy | 4'-methylbenzyl | 262–262.5 |
| 98 | n-butoxy | 4'-chlorobenzyl | 227–228.5 |
| 99 | benzyloxy | 4'-chlorobenzyl | 262–264 |

EXAMPLE 100.

4-Benzyl-3-(2'-furylmethylthio)-5-sulfamylbenzoic acid

3-Amino-4-benzyl-5-sulfamylbenzoic acid (6.1 g) and sodium nitrite (1.4 g) is dissolved in 2 N sodium hydroxide (22.5 ml) and the resulting solution is added dropwise to a mixture of acetic acid (15 ml) and conc. hydrochloric acid (15 ml), while stirring at −5° to 0° C.. The resulting diazonium solution is clarified by rapid filtration and is then added to a stirred solution of furfuryl mercaptan (3.3 ml) in 4 N sodium hydroxide (125 ml) in the presence of copper-powder (2.0 g). After additional stirring at room temperature for 1 hour, the mixture is heated on a steam bath for 2 hours to complete the nitrogen evolution. The mixture is then filtered hot in the presence of decolorizing carbon, and, after cooling, the filtrate is acidified with acetic acid (12 ml). The resulting precipitate is collected by filtration and washed with water. After drying, the material is dissolved in hot saturated sodium hydrogen carbonate (30 ml) and the solution is left in a refrigerator for 24 hours. The precipitated sodium 4-benzyl-3-(2'-furylmethylthio)-5-sulfamylbenzoate is collected by filtration, washed with a small amount of ice-cold water and dried. The salt is then dissolved in water (10 ml) and the 4-benzyl-3-(2'-furylmethylthio)-5-sulfamylbenzoic acid is precipitated by acidification with 1 N acetic acid (5 ml). The acid is collected by filtration and washed with water. After drying and recrystallization from aqueous ethanol, and acid is obtained with a melting point of 206°–207° C. (dec.).

EXAMPLE 101

4-Benzyl-3-benzylthio-5-sulfamylbenzoic acid

By replacing in Example 100, furfuryl mercaptan with an equimolar amount of benzyl mercaptan and following the procedure described, 4-benzyl-3-benzylthio-5-sulfamylbenzoic acid is obtained with a melting point of 222°–224° C.. The material is identical (IR, analysis) with the material prepared as in Example 85.

EXAMPLE 102

4-Benzyl-3-n-propylthio-5-sulfamylbenzoic acid

A. Ethylxanthic acid 2-benzyl-5-carboxy-3-sulfamylphenyl ester.

A solution of 3-amino-4-benzyl-5-sulfamylbenzoic acid (12.25 g) and sodium nitrite (2.8 g) in 2 N sodium hydroxide (50 ml) is dropwise added to a mixture of conc. hydrochloric acid (30 ml) and acetic acid (30 ml) while stirring at −5° C to 0° C. After additional stirring for about 15 minutes, the resulting diazonium solution is clarified by rapid filtration, and is then during about 15 minutes added to a solution of potassium ethyl xanthate (7.0 g) and sodium hydrogen carbonate (80 g) in water (250 ml) while stirring at 60°–70° C. After additional stirring at this temperature for 1 hour, the resulting solution is cooled, and is then acidified with conc. hydrochloric acid to precipitate ethylxanthic acid 2-benzyl-5-carboxy-3-sulfamylphenyl ester. The compound is collected by filtration, washed with water and dried.

B. 4-Benzyl-3-n-propylthio-5-sulfamylbenzoic acid.

A mixture of ethylxanthic acid 2-benzyl-5-carboxy-3-sulfamylphenyl ester (2.1 g), n-propylbromide (0.62 g) and dry ethylene diamine (10 ml) is stirred at 70° C for 4 hours in a nitrogen atmosphere. The resulting solution is poured into a mixture of conc. hydrochloric acid (35 ml) and ice (about 50 g). The precipitated material is collected by filtration, washed with water and dried. It is then dissolved in a hot saturated sodium hydrogen carbonate solution (25 ml) and filtered hot in the presence of decolorizing carbon. After cooling, the separated sodium 4-benzyl-3-n-propylthio-5-sulfamylbenzoate is collected by filtration and washed with a minor amount of icecold water. The dried sodium salt is dissolved in hot water (25 ml), and the 4-benzyl-3-n-propylthio-5-sulfamylbenzoic acid is precipitated by acidification with conc. hydrochloric acid (1 ml). After cooling, the acid is collected by filtration, washed with water and dried. After recrystallization from aqueous ethanol, the compound is obtained with a melting point of 205°–206° C. The material is identical (IR, analysis) with the material prepared as in Example 83.

EXAMPLE 103

4-Benzyl-3-benzylthio-5-sulfamylbenzoic acid

By replacing in Example 102, step B, n-propyl bromide with an equimolar amount of benzyl bromide and performing the reaction at room temperature for 20 hours, 4-benzyl-3-benzylthio-5-sulfamylbenzoic acid is obtained with a melting point of 222°–224° C. The material is identical (IR, analysis) with the material prepared as in Example 85.

EXAMPLE 104

4-Benzyl-3-ethylthio-5-sulfamylbenzoic acid

A. 4-Benzyl-3-mercapto-5-sulfamylbenzoic acid.

A mixture of ethylxanthic acid 2-benzyl-5-carboxy-3-sulfamylphenyl ester (prepared as described in Example 102, step A; 85 g) and 2 N sodium hydroxide (500 ml) is in a nitrogen atmosphere heated on a steam bath for 2 hours. After cooling, the resulting solution is added dropwise to 4 N hydrochloric acid (300 ml) while stirring in a nitrogen atomsphere, to precipitate crude 4-benzyl-3-mercapto-5-sulfamylbenzoic acid. The material is collected by filtration, washed with water and dried. It is then dissolved in diethyl ether, and the solution is clarified by filtration. The diethyl ether is removed in vacuo, and the residue is crystallized by trituration with water. The resulting 4-benzyl-3-mercapto-5-sulfamylbenzoic acid is collected by filtration, washed with water and dried.

B. 4-Benzyl-3-ethylthio-5-sulfamylbenzoic acid.

A mixture of 4-benzyl-3-mercapto-5-sulfamylbenzoic acid (1.0 g), sodium hydrogen carbonate (0.3 g), sodium dithionite (0.3 g), ethyl iodide (1.0 ml) and saturated sodium hydrogen carbonate solution (8 ml) is stirred at 70° C for 3 hours. After cooling, the precipitated sodium 4-benzyl-3-ethylthio-5-sulfamylbenzoate is collected by filtration and washed with a minor amount of icecold water. After drying, the sodium salt is dissolved in hot water (10 ml), and the solution is clarified by the filtration hot in the presence of decolorizing carbon. The solution is acidified with conc. hydrochloric acid (0.5 ml) to precipitate the 4-benzyl-3-ethylthio-5-sulfamylbenzoic acid. The acid is collected by filtration, washed with water and dried. After recrystallization from aqueous ethanol, the compound is obtained with a melting point of 234°–235° C.

EXAMPLE 105–115

By following the procedure described in Example 104, step B, but replacing ethyl iodide with equimolar amounts of other halogenides as defined in Table VII below, the corresponding 3-substituted 4-benzyl-5-sulfamylbenzoic acids of Table VII are obtained.

Table VII

| Ex. No. | Halogenide used in the reaction | 3-substituent | M.p. ° C. of 3-substituted-4-benzyl-5-sulfamylbenzoic acid. |
|---|---|---|---|
| 105 | methyl iodide | methylthio | 233–234 |
| 106 | n-butyl iodide | n-butylthio | 205–205.5 |
| 107 | n-pentyl bromide | n-pentylthio | 210–211 |
| 108 | allyl bromide | allylthio | 187–188 |
| 109 | 1-bromo-6-chlorohexane | 6-chlorohexylthio | 195–196 |
| 110 | 2-n-butylthio-ethyl chloride | (2-n-butylthio)ethylthio | 139–142 |
| 111 | 2-phenoxyethyl-bromide | 2-phenoxyethylthio | 143–145 |
| 112 | 3-methoxybenzyl-chloride | 3-methoxybenzylthio | 188–189 |
| 113 | 4-chloromethyl-pyridine, HCl | 4-pyridylmethylthio | 205–208 |
| 114 | 3-bromomethyl-thiophene | 3-thienylmethylthio | 186–187 |
| 115 | 4-chloromethyl-2-methylthiazole | 2-methylthiazolyl-(4)-methylthio | 200–202 |

The compounds prepared as in Examples 105 and 106 are identical (IR, analysis) with the compounds prepared as in Examples 82 and 84 respectively.

EXAMPLE 116

4-Benzyl-3-(4-pyridylethylthio)-5-sulfamylbenzoic acid

A mixture of 4-benzyl-3-mercapto-5-sulfamylbenzoic acid (3.25 g), sodium hydrogen carbonate (2.0 g), sodium dithionite (2.0 g), 4-vinylpyridine (1.5 ml) and saturated sodium hydrogen carbonate (33 ml) is stirred at 70° C. for 4 hours. After cooling, the mixture is acidified with 4 N acetic acid. The separated material is collected by filtration and washed with water. After drying and recrystallization twice from aqueous ethanol, 4-benzyl-3-(4-pyridylethylthio)-5-sulfamylbenzoic acid is obtained as a hemihydrate with a melting point of 180° –182° C..

EXAMPLE 117

4-Benzyl-3-(2′,3+-dibromo-n-propylthio)-5-sulfamylbenzoic acid.

To a stirred solution of 3-allylthio-4-benzyl-5-sulfamylbenzoic acid (1.65 g) in acetic acid (10 ml), a solution of bromine (0.3 ml) in acetic acid (6 ml) is added dropwise during about 15 minutes. After additional stirring for about 1 hour, water (20 ml) is added and the mixture is left in a refrigerator for about 20 hours. The resulting precipitate is collected by filtration and washed with water. After drying and recrystallization from aqueous ethanol, 4-benzyl-3-(2′,3′-dibromo-n-propylthio)-5-sulfamylbenzoic acid is obtained with a melting point of 205°–207° C.

EXAMPLE 118

4-Benzoyl-3-benzyloxy-5-sulfamylbenzoic acid

A. 4-Benzoyl-3-hydroxy-5-sulfamylbenzoic acid.

To a stirred mixture of conc. sulfuric acid (125 ml) and water (40 ml), 4-amino-6-carboxy-3-phenyl-1,2-benzisothiazole 1,1-dioxide (15.1 g) is added in portions. The resulting solution is cooled to 0°–5° C. and the amine is diazotized by the dropwise addition of a solution of sodium nitrite (3.8 g) in water (40 ml). The diazonium-mixture is then heated on a steam bath for 2–3 hours until the nitrogen evolution has ceased. After cooling and dilution with water (about 200 ml), the resulting precipitate is collected by filtration and washed with water. The material is dried and recrystallized twice from aqueous ethanol. The thus purified material is dissolved in 1 N sodium hydroxide and the solution is added to a slight excess of ice-cold 1 N hydrochloric acid. The resulting precipitate is collected by filtration, washed with water and dried in vacuo in the presence of $P_2O_5$ to give 4-benzoyl-3-hydroxy-5-sulfamylbenzoic acid as a hemihydrate.

B. 4-Benzoyl-3-benzyloxy-5-sulfamybenzoic acid.

To a solution of 4-benzoyl-3-hydroxy-5-sulfamylbenzoic acid hemihydrate (3.21 g) in 0.50 N NaOH (40.0 ml), benzyl bromide (1.2 ml) is added and the mixture is stirred at room temperature for 5 hours. The mixture is left in a refrigerator for about 16 hours, and the separated sodium 4-benzoyl-3-benzyloxy-5-sulfamylbenzoate is collected by filtration and washed with a small amount of ice-cold water. The salt is dissolved in 1 N sodium hydroxide (30 ml) and the solution is added to ice-cold 1 N acetic acid (35 ml). The resulting precipitate is collected by filtration and washed with water. After drying in vacuo in the presence of $P_2O_5$, 4-benzoyl-3-benzyloxy-5-sulfamylbenzoic acid is obtained. The material is identical (IR, analysis) with the material prepared as in Example 40.

EXAMPLES 119–120

By replacing in Example 118, step B, benzyl bromide with equimolar amounts of crotyl bromide and 3-bromoethylthiophene respectively and following the procedure described, 4-benzoyl-3-cr yloxy-5-sulfamylbenzoic acid and 4-benzoyl-5-sulfamyl-3-(3-thienylmethoxy)benzoic acid respectively are obtained.

EXAMPLES 121–123

After heating of the 3-substituted-4-benzoyl-5-sulfamylbenzoic acids described in Examples 118, step A, 119 and 120 for 10 minutes to 230°–235° C., 160–165° C. and 175°–180° C. respectively, 6-carboxy-4-hydroxy-3-phenyl-1,2-benzisothiazole 1,1-dioxide, 6-carboxy-4-crotyloxy-3-phenyl-1,2-benzisothiazole 1,1-dioxide and 6-carboxy-4-(3-thienylmethoxy)-3-phenyl-1,2-benzisothiazole 1,1-dioxide are obtained with melting points of 279°–281° C., 182°–184° C. and 193°–195° C. respectively.

EXAMPLE 124

Methyl 4-benzyl-3-n-butylthio-5-sulfamylbenzoate

A solution of 4-benzyl-3-n-butylthio-5-sulfamylbenzoic acid (0.85 g) in dry methanol (10 ml) and conc. sulfuric acid (0.2 ml) is refluxed for 20 hours. The methanol is removed in vacuo and the residue is triturated with 1 N sodium hydrogen carbonate (15 ml). The resulting crystalline material is collected by filtration, washed with water and dried. After recrystallization from methanol, methyl 4-benzyl-3-n-butylthio-5-sulfamylbenzoate is obtained with a melting point of 118°–120° C.

EXAMPLE 125

Methyl 4-benzyl-3-benzylthio-5-sulfamylbenzoate

By replacing in Example 124, 4-benzyl-3-n-butylthio-5-sulfamylbenzoic acid with 4-benzyl-3-benzylthio-5-sulfamylbenzoic acid and following the procedure described, methyl 4-benzyl-3-benzylthio-5-sulfamylbenzoate is obtained with a melting point of 139°–140° C.

EXAMPLE 126

Ethyl 4-benzyl-3-n-butylthio-5-sulfamylbenzoate

By replacing in Example 124, methanol with ethanol and following the procedure described, ethyl 4-benzyl-3-n-butylthio-5-sulfamylbenzoate is obtained with a melting point of 120°–122° C.

EXAMPLE 127

Ethyl 4-benzyl-3-benzylthio-5-sulfamylbenzoate

By replacing in Example 124, methanol with ethanol and 4-benzyl-3-n-butylthio-5-sulfamylbenzoic acid with 4-benzyl-3-benzylthio-5-sulfamylbenzoic acid and following the procedure described, ethyl 4-benzyl-3-benzylthio-5-sulfamylbenzoate is obtained with a melting point of 108°–110° C.

EXAMPLE 128

Cyanomethyl 4-benzyl-3-n-butylthio-5-sulfamylbenzoate

A mixture of 4-benzyl-3-n-butylthio-5-sulfamylbenzoic acid (0.78 g) chloroacetonitrile (0.17 g), triethylamine (0.42 g) and dry acetone (10 ml) is refluxed for 6 hours. After cooling, the separated triethylamine hydrochloride is removed by filtration, and the filtrate is evaporated in vacuo. The residue is crystallized by trituration with aqueous ethanol. After cooling the material is collected by filtration, washed with cold aqueous ethanol and dried. After recrystallization from aqueous ethanol, cyanomethyl 4-benzyl-3-n-butylthio-5-sulfamylbenzoate is obtained with a melting point of 112.5°–114° C.

EXAMPLE 129

Cyanomethyl 4-benzyl-3-benzylthio-5-sulfamylbenzoate

By replacing in Example 128, 4-benzyl-3-n-butylthio-5-sulfamylbenzoic acid with an equimolar amount of 4-benzyl-3-benzylthio-5-sulfamylbenzoic acid and following the procedure described, cyanomethyl 4-benzyl-3-benzylthio-5-sulfamylbenzoate is obtained with a melting point of 190.5°–192° C.

What we claim is:

1. A compound selected from the group of compounds of formula I

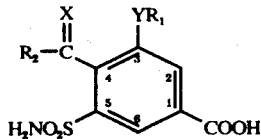

in which
$R_1$ is selected from the group consisting of methyl and ethyl radicals monosubstituted with thienyl;
$R_2$ stands for a phenyl radical, optionally being substituted with a member selected from the group consisting of halogen, lower alkyl, hydroxy and lower alkoxy;
Y stands for O;
X stands for a member selected from the group consisting of O and $H_2$; and pharmaceutically acceptable, non-toxic salts of the carboxylic acid of formula I.

2. A compound selected from the group of compounds of formula I

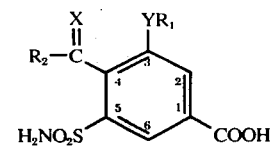

in which
$R_1$ is selected from the group consisting of methyl and ethyl radicals monosubstituted with thienyl;
$R_2$ stands for a phenyl radical;
Y stands for O;
X stands for a member selected from the group consisting of O and $H_2$;
and pharmaceutically acceptable, non-toxic salts of the carboxylic acid of formula I.

3. A compound selected from the group of compounds of formula I

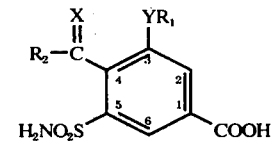

in which
$R_1$ is selected from the group consisting of methyl and ethyl radicals monosubstituted with thienyl;
$R_2$ stands for a phenyl radical, optionally being substituted with a member selected from the group consisting of halogen, lower alkyl, hydroxy and lower alkoxy;
Y stands for O;
X stands for O;
and the pharmaceutically acceptable, non-toxic salts of the carboxylic acid of formula I.

4. A compound selected from the group of compounds of formula I

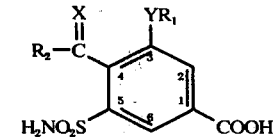

in which
$R_1$ is selected from the group consisting of methyl and ethyl radicals monosubstituted with thienyl;
$R_2$ stands for a phenyl radical;
Y stands for O;
X stands for O;
and the pharmaceutically acceptable, non-toxic salts of the carboxylic acid of formula I.

5. 4-Benzoyl-5-sulfamyl-3-(3'-thienylmethoxy)benzoic acid; and pharmaceutically acceptable, non-toxic salts of said carboxylic acid.

* * * * *